(12) United States Patent
Noon et al.

(10) Patent No.: US 11,844,553 B2
(45) Date of Patent: Dec. 19, 2023

(54) INTRAMEDULLARY BONE FIXATION DEVICE FOR RIBS

(71) Applicant: DePuy Synthes Products, Inc., Raynham, MA (US)

(72) Inventors: John M. Noon, Swarthmore, PA (US); Christopher Keegan, Hatboro, PA (US); Christian Peta, E. Fallowfield, PA (US); Albert Montello, Berwyn, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/931,141

(22) Filed: Sep. 12, 2022

(65) Prior Publication Data

US 2023/0083740 A1 Mar. 16, 2023

Related U.S. Application Data

(60) Provisional application No. 63/243,226, filed on Sep. 13, 2021.

(51) Int. Cl.
*A61B 17/72* (2006.01)
*A61B 17/16* (2006.01)
*A61B 17/00* (2006.01)

(52) U.S. Cl.
CPC ...... *A61B 17/7208* (2013.01); *A61B 17/1693* (2013.01); *A61B 17/7258* (2013.01);
(Continued)

(58) Field of Classification Search
CPC ............ A61B 17/7208; A61B 17/1693; A61B 17/7258; A61B 2017/00004; A61B 2017/00407; A61B 2017/00951
(Continued)

(56) References Cited

U.S. PATENT DOCUMENTS 6,053,922 A  4/2000 Krause et al.
6,447,518 B1 9/2002 Krause et al.
(Continued)

FOREIGN PATENT DOCUMENTS

CN 205626075 U 10/2016
EP 0689800 A2 1/1996
(Continued)

*Primary Examiner* — Eduardo C Robert
*Assistant Examiner* — David C Comstock
(74) *Attorney, Agent, or Firm* — BakerHostetler (57) ABSTRACT

An intramedullary bone fixation device that includes a shaft with a flexible region. The flexible region may be configured to flex from a first shape to a second shape as the shaft moves along a curved medullary canal. For example, the bone fixation device may include a distal bone screw that is configured to move along the curved medullary canal of first and second segments of a fractured bone (e.g., two segments of a broken rib) and fasten to the segment bone segment. The bone fixation device may include a locking member (e.g., a proximal bone screw) that is configured to lock the shaft to the first bone segment. For example, the shaft may be fixed to the distal bone screw and ratchetably coupled to the shaft such that the first and second bone segments can be compressed together by urging together the distal bone screw and the locking member.

20 Claims, 7 Drawing Sheets

(52) U.S. Cl.
CPC .............. *A61B 2017/00004* (2013.01); *A61B 2017/00407* (2013.01); *A61B 2017/00951* (2013.01)

(58) Field of Classification Search
USPC .......... 606/62, 105, 304, 314, 319, 320, 323
See application file for complete search history.

(56) References Cited

U.S. PATENT DOCUMENTS

| | | | |
|---|---|---|---|
| 7,785,355 B2 | 8/2010 | Mohr et al. | |
| 8,740,903 B2 | 6/2014 | Bottlang et al. | |
| 9,155,574 B2 | 10/2015 | Saravia et al. | |
| 2008/0147126 A1 | 6/2008 | Tipirneni et al. | |
| 2013/0012942 A1 | 1/2013 | Nelson et al. | |
| 2014/0114312 A1* | 4/2014 | Krause | A61B 17/864 606/62 |
| 2015/0374411 A1* | 12/2015 | Ehmke | A61B 17/686 606/329 |
| 2017/0079699 A1* | 3/2017 | Fallin | A61B 17/7225 |
| 2017/0189085 A1 | 7/2017 | Krause | |
| 2018/0317982 A1 | 11/2018 | Giordano et al. | |
| 2019/0120282 A1* | 4/2019 | Krause | F16C 1/04 |
| 2019/0282280 A1 | 9/2019 | Harshman et al. | |
| 2020/0054372 A1 | 2/2020 | Stinson et al. | |
| 2020/0093523 A1* | 3/2020 | Sinnott | A61B 17/1725 |
| 2020/0375853 A1 | 12/2020 | Briggs et al. | |
| 2021/0386461 A1 | 12/2021 | Briggs et al. | |
| 2022/0240997 A1* | 8/2022 | Krause | A61B 17/1631 |

FOREIGN PATENT DOCUMENTS

| | | |
|---|---|---|
| WO | 2007/009123 A2 | 1/2007 |
| WO | 2013/063145 A1 | 5/2013 |
| WO | 2020/077337 A1 | 4/2020 |
| WO | 2020/077457 A1 | 4/2020 |
| WO | 2020/081855 A1 | 4/2020 |

\* cited by examiner

INTRAMEDULLARY BONE FIXATION DEVICE FOR RIBS

CROSS-REFERENCE TO RELATED APPLICATIONS

This Application claims the benefit of U.S. Provisional Application Ser. No. 63/243,226 filed Sep. 13, 2021, the contents of which is hereby incorporated by reference as if set forth in its entirety herein.

TECHNICAL FIELD

The present invention relates to bone fixation devices, particularly to intramedullary rib fixation devices, and related methods.

BACKGROUND

Bone fixation devices can provide for fixation of adjacent segments of a broken bone (e.g., a rib). Rib splints, for example, can fix two adjacent portions of a rib together. However, rib splints and other rib fixation devices can be rigid and unable to be safely inserted within a medullary canal of the rib due to a curvature of the medullary canal. For example, if such rigid rib fixation devices are inserted into the rib's curved medullary canal, a distal end of such devices could break through the rib's cortical wall. Breaking through the cortical wall can result in damage to a patient (e.g., damage to soft tissue, the spinal cord, or organs).

SUMMARY

The present disclosure provides an intramedullary bone fixation device that includes a shaft with a flexible region. The flexible region may be configured to flex from a first shape to a second shape as the shaft moves along a curved medullary canal. For example, the intramedullary bone fixation device may include a distal bone screw that is configured to move along the curved medullary canal of first and second segments of a fractured bone (e.g., two segments of a broken rib) and fasten to the second bone segment. The intramedullary bone fixation device may include a locking member (e.g., a proximal bone screw) that is configured to lock the shaft to the first bone segment. For example, the shaft may be fixed to the distal bone screw and ratchetably coupled to the shaft such that the first and second bone segments can be compressed together by urging together the distal bone screw and the locking member.

When the first and second bone segments are compressed together, the distal bone screw and the locking member may fix the shaft to the first and second bone segments such that the first and second bone segments are fixed to one another. Thus, the first and second bone segments may be prevented from moving apart from one another.

According to an embodiment of the present disclosure, an intramedullary bone fixation device includes a shaft having a leading end and a trailing end opposite the leading end. The intramedullary bone fixation device includes a bone screw that extends from the leading end of the shaft. The bone screw is configured to move along a curved medullary canal of a bone. The shaft has a flexible region between the leading end and the trailing end, and the flexible region is configured to flex from a first shape to a second shape as the bone screw moves along the curved medullary canal.

According to another embodiment of the present disclosure, a method of securing first and second bone segments together includes driving a leading end of a bone fixation device through a first portion of a curved medullary canal that is defined by the first bone segment. The method includes driving a leading end of a bone fixation device through a second portion of the curved medullary canal that is defined by the second bone segment. The method includes causing a shaft, of the bone fixation device, with a flexible segment to flex from a first shape to a second shape during the driving step. The method include fixing the leading end to the second bone segment.

BRIEF DESCRIPTION OF THE DRAWINGS

The foregoing summary, as well as the following detailed description of illustrative embodiments of the intramedullary bone fixation device of the present application, will be better understood when read in conjunction with the appended drawings. For the purposes of illustrating the intramedullary bone fixation device of the present application, there is shown in the drawings illustrative embodiments. It should be understood, however, that the application is not limited to the precise arrangements and instrumentalities shown. In the drawings.

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Figures 1, 2:
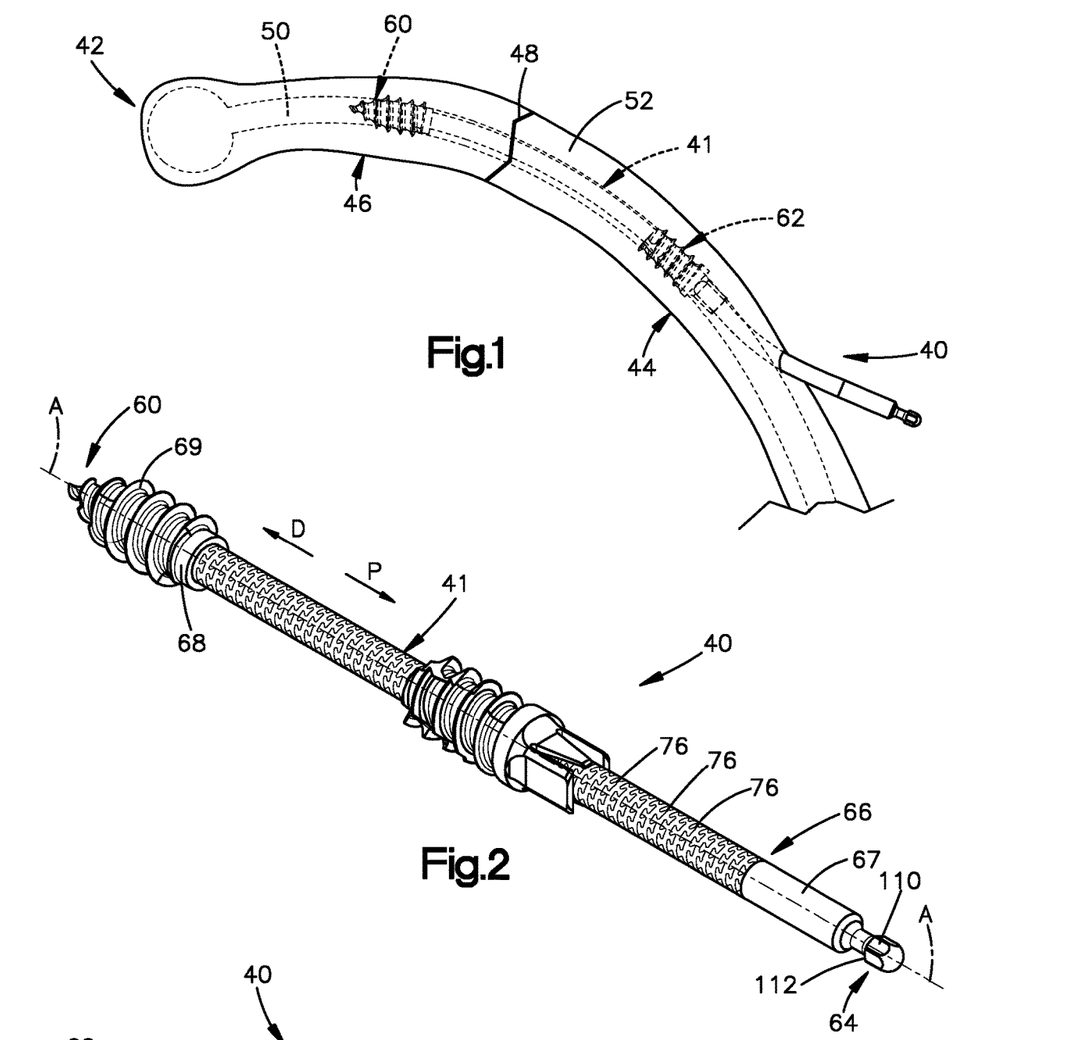
FIG. 1 is an oblique view of an intramedullary bone fixation device partially disposed inside of a medullary canal of a rib.
FIG. 2 is an oblique view of the intramedullary bone fixation device of FIG. 1.

Referring to FIG. 1, an intramedullary bone fixation device 40 with a flexible region 41 is illustrated in combination with a fractured rib 42. The fractured rib 42 includes first and second rib segments 44 and 46 (an example of first and second bone segments) that are separated by a fracture 48. The intramedullary bone fixation device 40 may fix the first and second rib segments 44 and 46 together.

For example, the intramedullary bone fixation device 40 may extend within a medullary canal 50, of the fractured rib 42, defined by a cortical wall 52 of the fractured rib 42 (the medullary canal 50 and portions of the intramedullary bone fixation device 40 disposed within the medullary canal 50 are illustrated with broken lines). The intramedullary bone fixation device 40 may include a leading end 60 configured to drive into the portion of the medullary canal formed by the second rib segment 46, and a locking member 62 configured to drive into a portion of the medullary canal formed by the first rib segment 44.

The leading end 60 may attach to a portion of the cortical wall formed by the second rib segment 46. The flexible region 41 may change its shape due to the curvature of the medullary canal 50, such that the leading end 60 remains within the medullary canal 50 when driving into the second rib segment 46. The locking member 62 may attach to a portion of the cortical wall formed by the first rib segment 44, thereby preventing the first and second rib segments 44 and 46 from separating from one another.

A trailing end 64 of the intramedullary bone fixation device 40 may extend out of the fractured rib 42. In some embodiments, the entirety of the intramedullary bone fixation device 40 is disposed within the fractured rib 42. For example, the intramedullary bone fixation device may be configured to entirely fit within the fractured rib when fully inserted. In an embodiment, the entire portion of the intramedullary bone fixation device extending outside of the fractured rib may be removed (e.g., by cutting off the portion extending outside of the rib).

During use, the lead end 60 of the intramedullary bone fixation device 40 may drive through a portion of the cortical wall 52 formed by the first rib segment 44 and follow the medullary canal 50 into the second rib segment 46. As the lead end 60 moves through the medullary canal, the flexible region 41 changes it shape such that the shape substantially matches the curvature of the medullary canal 50.

When the lead end 60 is disposed within and fixed to the second rib segment 46, the locking member 62 may be moved along the flexible region 41 and attached to the first rib segment 44 such that the first and second rib segments 44 and 46 are compressed together. For example, the flexible region 41 may be under tension when the locking member is attached to the flexible region 41 and the first rib segment 44.

In some embodiments, the entire intramedullary bone fixation device is made of cobalt-chrome and/or titanium.

Figure 3:
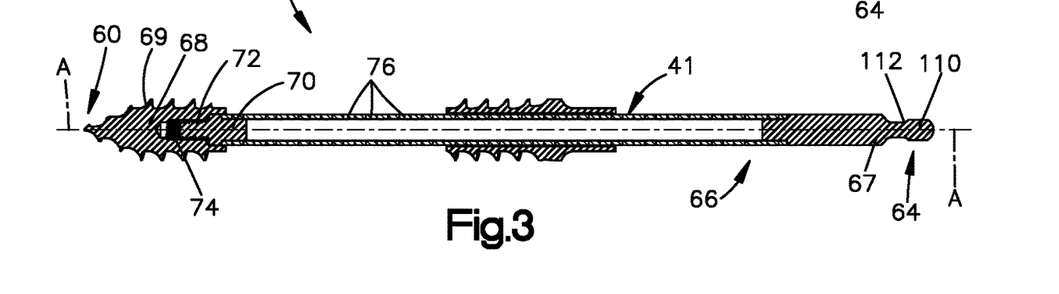
FIG. 3 is a cross-sectional side view of the intramedullary bone fixation device of FIG. 1.

Turning to FIGS. 2 and 3, the intramedullary bone fixation device 40 extends along a longitudinal axis A. The leading end 60 is spaced from the trailing end 64 in a distal direction D that extends along the longitudinal axis A opposite a proximal direction P.

When the intramedullary bone fixation device 40 is deployed (e.g., in the fractured rib 42 (FIG. 1), the longitudinal axis A may be curved to match the curvature of the flexible region 41. For example, the flexible region 41 may change its shape to accommodate the curvature of the medullary canal 50 (FIG. 1) and/or entry angles of the intramedullary bone fixation device 40 into the fractured rib 42 (FIG. 1).

The flexible region 41 formed by a shaft 66 of the intramedullary bone fixation device 40. For example, the shaft 66 may include the flexible region 41 and a tool engagement portion 67 attached to a proximal end of the flexible region 41. In an embodiment, the entirely of the shaft is the flexible region.

A distal end of the flexible region 41 may be fixed relative to the leading end 60. For example, the intramedullary bone fixation device 40 may include a distal bone screw 68 that forms the leading end 60. The distal bone screw 68 may be configured to ream cancellous bone of the fractured rib 42 and purchase with the cancellous bone and/or the cortical wall 52 (FIG. 1). For example, the distal bone screw 68 may be tapered at its distal end and may include radially outward helical threading 69 for threadedly purchasing within the portion of the cancellous bone and/or the cortical wall 52 formed by the second rib segment 46 (FIG. 1). The intramedullary bone fixation device 40 may include an attachment body 70 that attaches to a distal end (also referred to as a leading end) of the shaft 66 and the distal bone screw 68 such that the distal end of the shaft is axially and rotatably fixed to the distal bone screw 68. For example, the attachment body 70 may be press fit to a distal end of the shaft 66 and may include threads 72 that engage threads 74 of the distal bone screw 68. In some embodiments, the attachment body attaches to the shaft and the distal bone screw in a different manner, such as by welding the attachment body directly to the shaft. In some embodiments, the distal bone screw is attached directly to the shaft, such as by welding.

The tool engagement portion 67 may be configured to transmit torque to the distal bone screw 68 via the flexible region 41. For example, the flexible region 41 may comprise multiple laser cut segments 76 that interlock with one another. The flexible region 41 may be formed by a flexible shaft as disclosed in U.S. Pat. No. 6,053,922 entitled "Flexible shaft" or U.S. Pat. No. 6,447,518 entitled "Flexible shaft components," both of which are hereby incorporated by reference in their entirety. In some embodiments, the segments are formed in a manner other than laser cutting.

Figure 4:
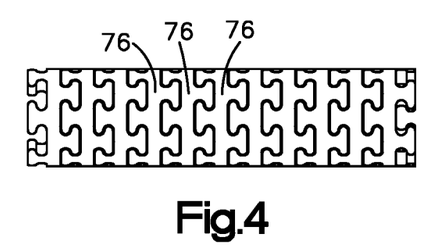
FIG. 4 is a side view of a shaft of the intramedullary bone fixation device of FIG. 1, shown in a straight configuration.
Figure 5:
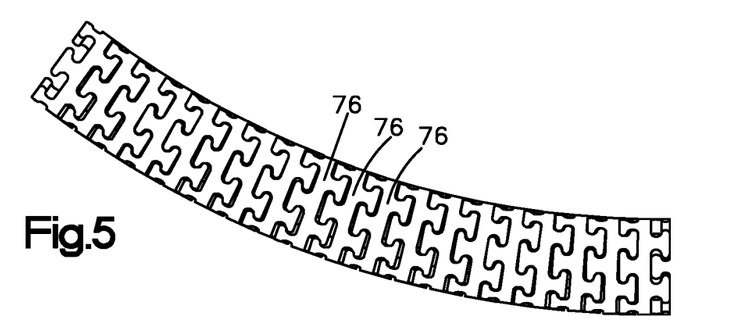
FIG. 5 is a side view of the shaft of FIG. 4, shown in a curved configuration.
Figure 6:
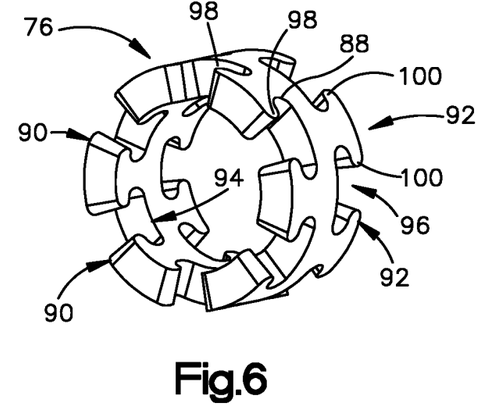
FIG. 6 is an oblique view of a laser cut segment of the shaft of FIG. 4.

Turning to FIGS. 4-6, each of the laser cut segments 76 may be configured such that adjacent laser cut segments 76 can pivot a limited amount relative to one another, and not separate from one another. For example, as shown in FIG. 6, each laser cut segment 76 includes a ring 88 and multiple distally facing connectors 90 extending distally from the ring 88 and multiple proximally facing connectors 92 extending proximally from the ring 88. In some embodiments, laser cut segments defining a distal end of the flexible region do not include proximally facing connectors and/or laser cut segments defining a proximal end of the flexible region do not include distally facing connectors.

The ring 88 may have a radially inner diameter of anywhere from 0.5 millimeter (mm) to 5.0 mm, preferably 1.55 mm. The ring may have a radially outer diameter of anywhere from 1.5 mm to 6.0 mm, preferably 2.55 mm. In some embodiments, the inner diameter is larger than 5.0 mm and/or the outer diameter is larger than 6.0 mm. For example, in cases where the shaft is implanted into a large bone (e.g., a femur).

Each laser cut segment may extend along the longitudinal axis A 0.25 millimeter (mm) to 2.0 mm, preferably 0.75 mm. The laser cut segments 76 may have a laser cut kerf width of 0.01 millimeters (mm) to 0.25 mm, preferably 0.10 mm.

The distally facing connectors 90 of a given laser cut segment 76 are configured to interlock with the proximally facing connectors 92 of an adjacent laser cut segment 76, as shown in FIGS. 4 and 5. For example, the connectors 90 and 92 may be formed in a diametrical pattern.

Each laser cut segment 76 may include six distally facing connectors 90 and six proximally facing connectors 92 that are circumferentially offset from corresponding distally facing connectors 90. In an embodiment, each laser cut segment includes more than or less than six distally facing connectors and/or more than or less than six proximally facing connectors. For example, each laser cut segment may include anywhere from three to eleven distally facing connectors and three to eleven proximally facing connectors.

Adjacent connectors 90 and 92 may define a connector receptacle 94 or 96. For example, the connectors 90 and 92 may each include a circumferentially extending protrusions 98 or 100 such that connectors 90 or 92 disposed within corresponding connector receptacles 94 or 96 are retained within such connector receptacles 94 or 96.

Figure 7:
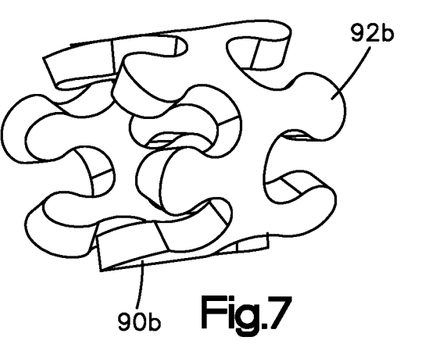
FIG. 7 is an oblique view of a laser cut segment according to a second embodiment of the shaft of FIG. 4.
Figure 8:
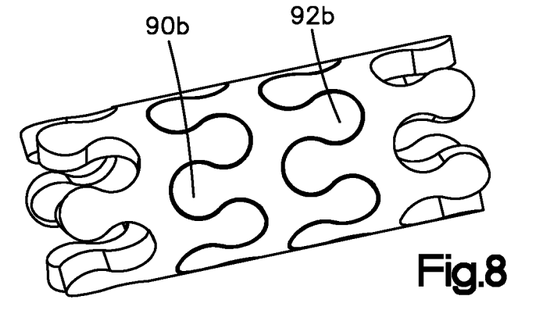
FIG. 8 is a side view of multiple laser cut segments of FIG. 7 interconnected to form a portion of the shaft.
Figure 9:
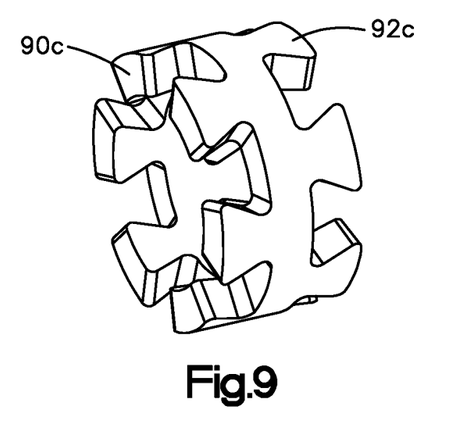
FIG. 9 is an oblique view of a laser cut segment according to a third embodiment of the shaft of FIG. 4.
Figure 10:
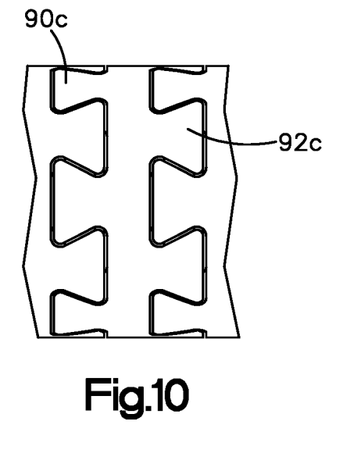
FIG. 10 is a side view of multiple laser cut segments of FIG. 9 interconnected to form a portion of the shaft.
Figure 11:
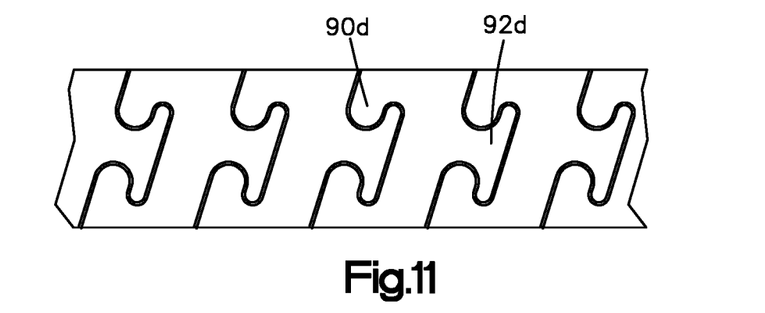
FIG. 11 is a side view of multiple intercut laser cut segments according to a fourth embodiment of the shaft of FIG. 4 to form a portion of the shaft.

For example, the connectors 90 and 92 may define a "T" shape such that adjacent connectors 90 or 92 define a connector receptacle 94 or 96 that has a "T" shape that the corresponding connector 90 or 92 is disposed within. In some embodiments, different connector shapes can be used. For example, bulb shaped connectors 90b and 92b as shown in FIGS. 7 and 8, dovetail shaped connectors as shown in FIGS. 9 and 10. In some embodiments, the connectors may be helically cut (e.g., "T" shaped connectors 90d and 92d as shown in FIG. 11).

Forming the shaft 66 (FIG. 2) may include providing a hollow tube and laser cutting the tube to form each connector 90 and 92 and connector receptacle 94 and 96. For example, the hollow tube may be a single piece tube that forms the radially interior and exterior profiles of the shaft 66.

In an embodiment, the entire intramedullary bone fixation device is formed of interconnected laser cut segments. For example, the distal bone screw, the shaft, and the locking member may each be formed of laser cut segments such that the distal bone screw, the shaft, and the locking member each include a respective flexible segment that is configured to follow the curvature of the medullary canal.

Referring again to FIGS. 2 and 3, the tool engagement portion 67 may include a male tool connector 110 that is configured to receive a tool (e.g., a socket, not shown) to transmit torque from the tool to the distal bone screw 68. The male tool connector 110 may form a shoulder 112 that is configured to receive a tensioning force from a tensioning tool. In some embodiments, the intramedullary bone fixation device 40 includes different tool engagement portions.

Figure 12:
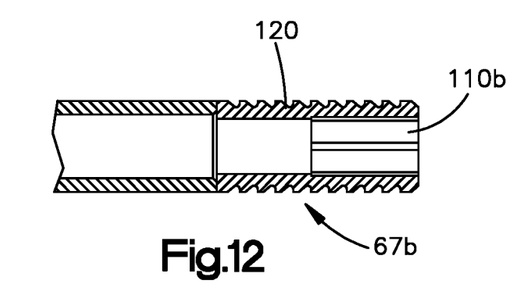
FIG. 12 is a cross-sectional side view of a second embodiment of a proximal end of the shaft of FIG. 4.
Figure 13:
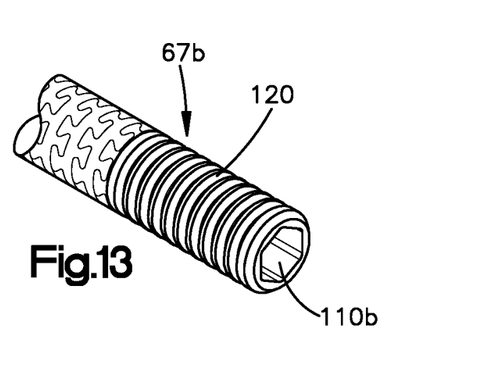
FIG. 13 is an oblique view of the proximal end of FIG. 12.

Turning to FIGS. 12 and 13, for example, the intramedullary bone fixation device 40 may include a tool engagement portion 67b that includes a socket tool connector 110b configured to receive a male connector of a tool (e.g., a drill or screw driver). The tool engagement portion 67b may include a radially outer ribbed section 120 that is configured to engage with the locking member 62 and/or a tensioning tool (not shown). The radially outer ribbed section 120 may extend axially along a majority of the tool engagement portion 67b. For example, the radially outer ribbed section 120 may axially overlap the socket tool connector 110b.

Figure 14:
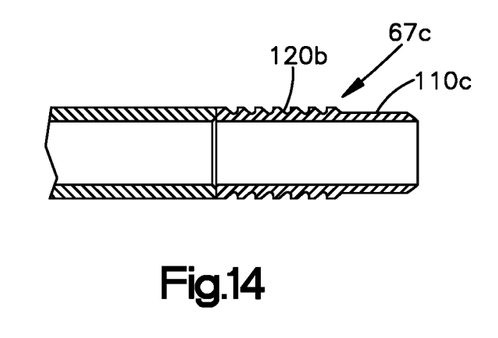
FIG. 14 is a cross-sectional side view of a third embodiment of a proximal end of the shaft of FIG. 4.
Figure 15:
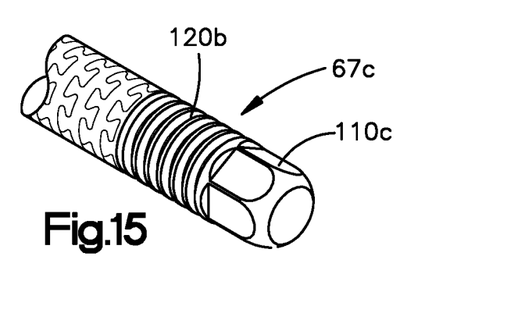
FIG. 15 is an oblique view of the proximal end of FIG. 14.

Turning to FIGS. 14 and 15, as another example, the intramedullary bone fixation device 40 may include a tool engagement portion 67c that includes a male tool connector 110c and a radially outer ribbed section 120b that is axially offset from the male tool connector 110c. For example, the radially outer ribbed section 120b may extend proximally from the male tool connector 110c.

In an embodiment, a resorbable or non-resorbable adhesive or polymer is inserted within the shaft to lock the shaft in place in the medullary canal, thereby fixing the first and second rib segments 44 and 46 together (FIG. 1). The resorbable adhesive may be an injectable polymer (e.g., cyanoacrylate, calcium phosphate, or poly (L/DL-lactide)). For example, the RAPIDSORB® injectable polymer system may be used to inject the adhesive into the proximal end of the shaft 66 via proximal openings in the tool engagement portions 67b and 67c described with reference to FIGS. 12-15.

During injection the resorbable adhesive may flow through the shaft and out recesses formed between adjacent laser cut segments to fill space between the shaft and first and second rib segments. In some embodiments, the tool engagement portion is removed or not present such that the adhesive is insertable into a proximal opening in the shaft to secure the first and second rib segments with the adhesive.

Figure 16:
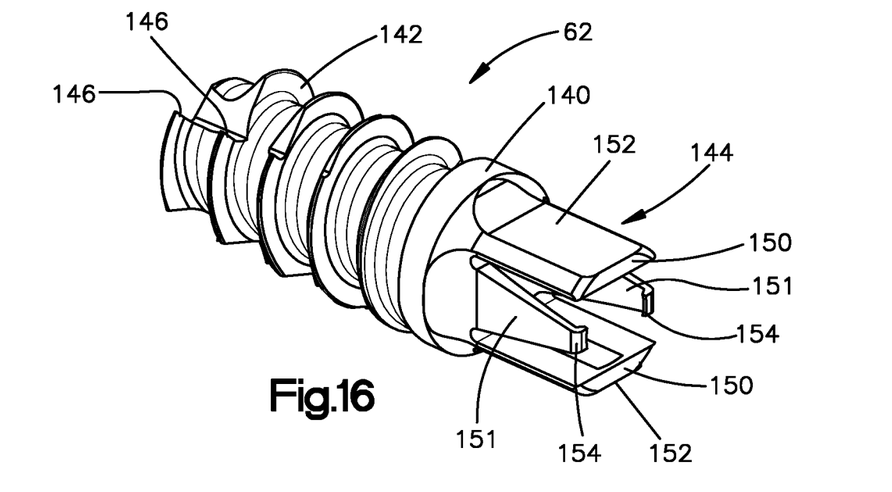
FIG. 16 is an oblique view of a proximal locking member of the intramedullary bone fixation device of FIG. 1.
Figure 17:
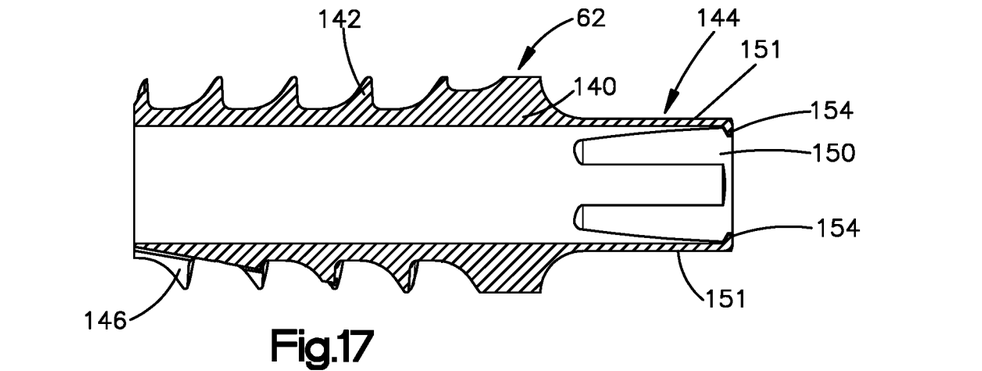
FIG. 17 is a cross-sectional side view of the proximal locking member of FIG. 16.

Turning to FIGS. 16 and 17, the locking member 62 may include a main body 140 with a tubular shape, radially outer helical threading 142 extending from the main body 140, and an engagement section 144 extending proximally from the main body 140. The radially outer helical threading 142 may include thread cutting surfaces 146 that are configured to cut threading into the cortical wall (FIG. 1).

The engagement section 144 may include a pair of engagement members 150 and/or a pair of ratcheting arms 151. The engagement members 150 may extend distally from the main body 140 to form tool engagement surfaces 152 that are configured to receive a tool (e.g., socket). The engagement surfaces 152 may be oriented diametrically opposed to one another. For example, the engagement surfaces 152 are flat and face away from one another.

The ratcheting arms 151 may be configured to lock against the shaft 66 (FIG. 1) such that the locking member is only movable proximally and not distally along the shaft 66 when the ratcheting arms are engaged with the shaft 66 (i.e., when the locking member 62 is in a locked position). For example, each distal end of the ratcheting arms 151 may include a radially inwardly extending protrusion 154 that is configured to engage recesses of the shaft 66 (e.g., spaces between adjacent laser cut segments shown in FIG. 2 and/or spaces between adjacent ribs of the radially outer ribbed sections 120*b* or shown in FIGS. 12-15). The radially inwardly extending protrusions 154 may extend radially toward one another (e.g., directly toward one another).

When in an unlocked position, the locking member 62 is configured to move proximally along the shaft 66 (FIG. 1). For example, the ratcheting arms 151 can be moved radially away from one another such that the locking member 62 is in the locked position. In some embodiments, a tool urges the ratcheting arms 151 apart from one another to transition the locking member 62 into the unlocked position.

Referring now to FIGS. 1, 2, and 16, when the shaft 66 is disposed within the medullary canal 50 and spans the fracture 48, as discussed above, the locking member 62 may be moved distally along the shaft 66. The locking member 62 may move distally when in the locked position such that the radially inwardly extending protrusions 154 are disposed within recesses of the shaft (e.g., space between adjacent laser cut segments 76). For example, a user may urge the shoulder 112 proximally while urging the locking member 62 distally (e.g., with a tool) to axially compress together the first and second rib segments 44 and 46. When the first and second rib segments 44 and 46 are compressed together, the shaft 66 may be under tension between the lead end 60 and the locking member 62.

Figure 18:
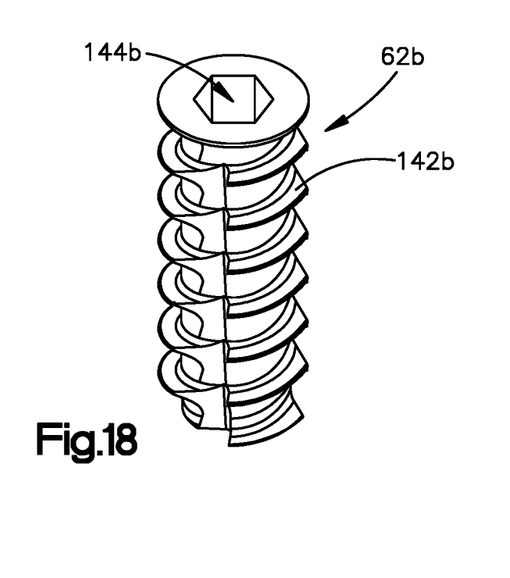
FIG. 18 is an oblique view of a second embodiment of the locking member of FIG. 17.

In some embodiments, the intramedullary bone fixation device 40 includes a different locking member. For example, the intramedullary bone fixation device 40 may include a locking member 62*b*, as shown in FIG. 18, which includes radially outer helical threading 142*b* and an engagement section 144*b* configured to receive a male end of a tool to rotate the locking member 62*b*. The locking member 62*b* may be configured to engage the shaft 66 (FIG. 1) such that the locking member 62*b* is not moveable proximally when in a locked position. For example, the locking member 62*b* may include radially inwardly extending protrusions to engage recesses of the shaft 66 (FIG. 1). In an embodiment, the locking member 62*b* includes collet type slots to cinch onto the shaft.

Figure 19:
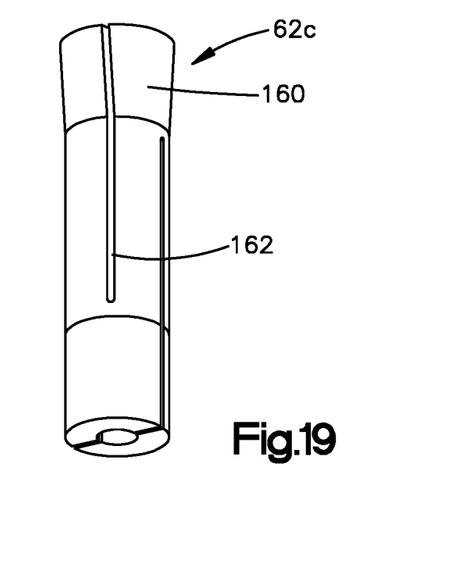
FIG. 19 is an oblique view of a third embodiment of the locking member of FIG. 17.

In another example, the intramedullary bone fixation device 40 may include a locking member 62*c* that includes a proximal end forming an axially outwardly inclined surface 160 and is configured to cinch to the shaft 66 (FIG. 1). For example, the locking member 62*c* may include collet type slots 162 that extend axially such that the proximal end of the locking member 62*c* moves radially inwardly toward the shaft 66 as the axially outwardly inclined surface 160 moves distally against the cortical wall 52 (FIG. 1). The locking member 62*c* may include radially inwardly extending protrusions to engage recesses of the shaft 66, such that the locking member 62*b* is not moveable proximally when in a locked position.

In some embodiments, the locking member may include one or more bone screws that are oriented transversely to the shaft, instead of coaxially with the shaft. For example, the locking member may include a pair of bone screws that extend transversely through the cortical wall formed by the first rib segment 44 to transversely engage the shaft with the tips of the pair of bone screws, when the shaft is within the medullary canal 50. Each of the pair of bone screws may engage portions of the shaft that are axially offset from one other.

Figure 20:
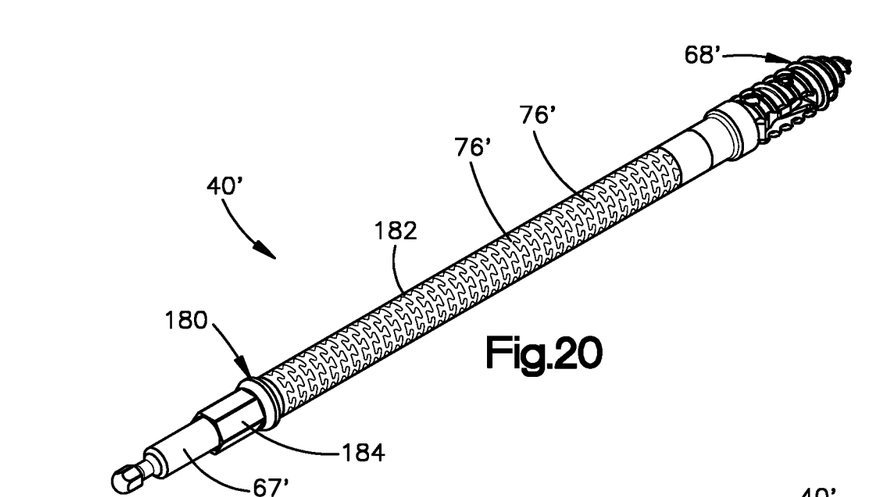
FIG. 20 is an oblique view of a second embodiment of the intramedullary bone fixation device of FIG. 1, including distal expandable locking members.
Figures 21, 22:
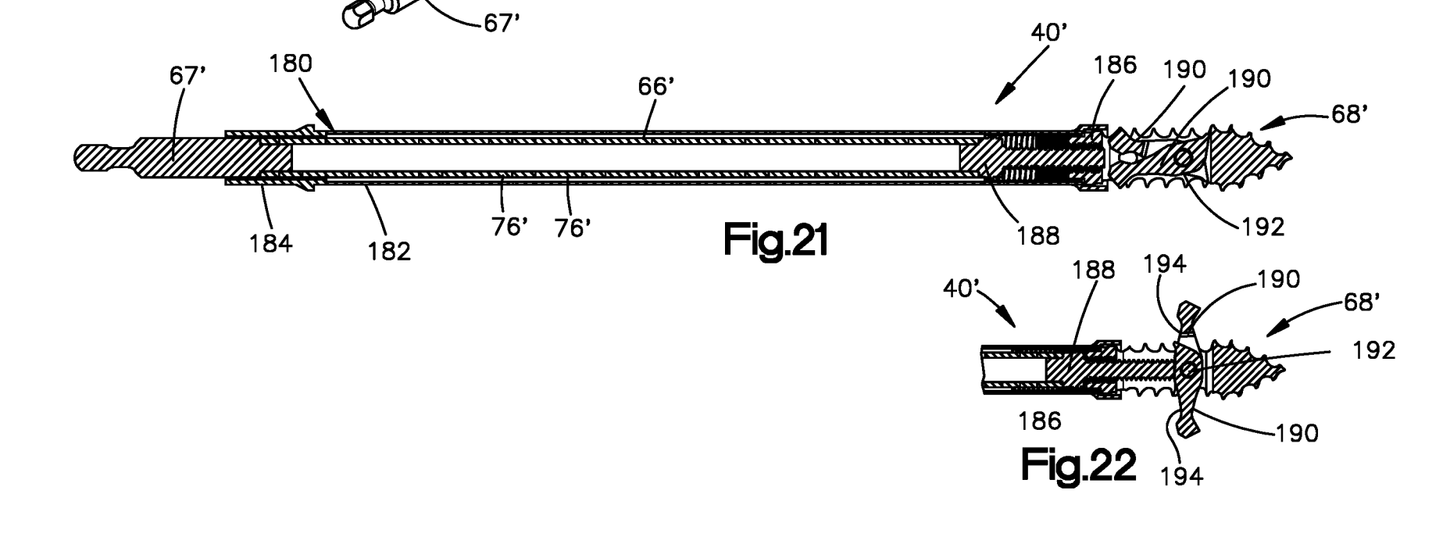
FIG. 21 is a cross-sectional side view of the intramedullary bone fixation device of FIG. 20.
FIG. 22 is a cross-sectional side view of the distal end of the intramedullary bone fixation device of FIG. 21, in an expanded configuration.

Referring now to FIGS. 20-22, a second embodiment of the intramedullary bone fixation device is shown. It is to be appreciated that the second embodiment can be similar to the first embodiment of the intramedullary bone fixation device shown in FIGS. 1-4. Accordingly, the same reference numbers used above with reference to the first embodiment can be also used with a "prime" notation in reference to a second embodiment. It is also to be appreciated that, unless otherwise set forth below, the components (and features thereof) of the intramedullary bone fixation device 40' of the second embodiment can be similar to those of the first embodiment.

Referring to FIGS. 20 and 21, the intramedullary bone fixation device 40' may include an inner shaft 66' (shown in FIG. 21), a tool engagement portion 67', a distal bone screw 68', and an outer shaft 180. A distal end of the outer shaft 180 may be configured to rotatably fix to the distal bone screw 68' such that rotation of the outer shaft 180 rotates the distal bone screw 68'.

The outer shaft 180 may include a flexible region 182 and a proximal tool engagement portion 184. The flexible region 182 may be configured in a similar manner as the flexible region 41 to change its shape to accommodate curvature of the medullary canal 50 (FIG. 1). For example, the flexible region 182 may include multiple laser cut segments 76'.

The proximal tool engagement portion 184 is configured to receive a tool (e.g., a socket, not shown). The proximal tool engagement portion 184 may be rotatably fixed to a proximal end of the flexible region 182 such that the tool engagement portion 184 is configured to transmit torque to the distal bone screw 68' via the flexible region 182.

Referring now to FIGS. 21 and 22, the distal bone screw 68' may be radially expandable. For example, the distal bone screw 68' may include a main body 186, a camming bolt 188, and camming arms 190. The camming arms 190 may be rotatably coupled to the main body 186 such that the camming arms 190 are rotatable from a retracted position shown in FIG. 21 to an expanded position shown in FIG. 22. For example, the camming arms 190 may be coupled to a pin 192 that extends transversely (e.g., perpendicular to) the longitudinal axis A (FIG. 2).

The camming bolt 188 may be configured to drive the camming arms 190 from the retracted position to the expanded position. For example, the camming bolt 188 may be rotatably coupled to the inner shaft 66' and threadedly coupled to the main body 186 such that rotation of the camming bolt 188 in a first direction causes the camming bolt 188 to translate distally toward the camming arms 190. The camming bolt 188 may be configured to engage corresponding camming surfaces 194 of the camming arms 190 such that translating the camming bolt 188 distally against the camming surfaces 194 causes the camming arms 190 to rotate into the expanded position.

During use, the distal bone screw 68' may be inserted into the medullary canal in a similar manner as the distal bone screw 68. For example, the tool engagement portion 184 may be rotated to rotate the distal bone screw 68' via the flexible region 182, thereby driving the distal bone screw 68' along the medullary canal. As the distal bone screw 68' moves through the medullary canal, the inner shaft 66' and the outer shaft 180 changes their respective shape such that each shape substantially matches the curvature of the medullary canal 50 (FIG. 1), in a similar manner as the flexible region 41 discussed above.

When the distal bone screw 68' is disposed within and fixed to the second rib segment 46 (FIG. 1), the tool engagement portion 67' may be rotated to rotate the camming bolt 188 via the inner shaft 66', thereby distally translating the camming bolt 188 against the camming surfaces 194. Distally translating the camming bolt 188 against the camming surfaces 194 causes the camming arms 190 to rotate about the pin into the expanded position. When in the expanded position, the camming arms 190 may engage with the cortical wall 52 to rotatably and/or axially fix the distal bone screw 68' to the cortical wall.

In an embodiment, the outer shaft can be removed from the medullary canal separately from the inner shaft and the distal bone screw, before or after the camming arms are moved into the locked position. For example, the outer shaft can be unscrewed from the camming bolt and moved proximally out of the medullary canal before the camming bolt 188 is rotated to move the camming arms into the locked position.

A locking member (e.g., locking member 62 discussed above) may be moved along the inner shaft 66' in a similar manner as discussed above with reference to FIG. 1 and the flexible region 41.

In an embodiment, the camming bolt may threadedly purchase with the outer shaft. For example, a proximal end of the camming bolt may have external threads that purchase with internal threading of the outer shaft proximally of the main body of the distal bone screw.

In some embodiments, the intramedullary bone fixation device includes a retraction mechanism configured to retract the camming arms. For example, a wire may be attached to each free end of the camming arms and configured to retract the camming arms when the wire is pulled proximally. For example, each wire may extend proximally from the camming arms, through the inner shaft, to the trailing end of the intramedullary bone fixation device such that a user can pull the wires to retract the camming arms.

Figures 23, 24:
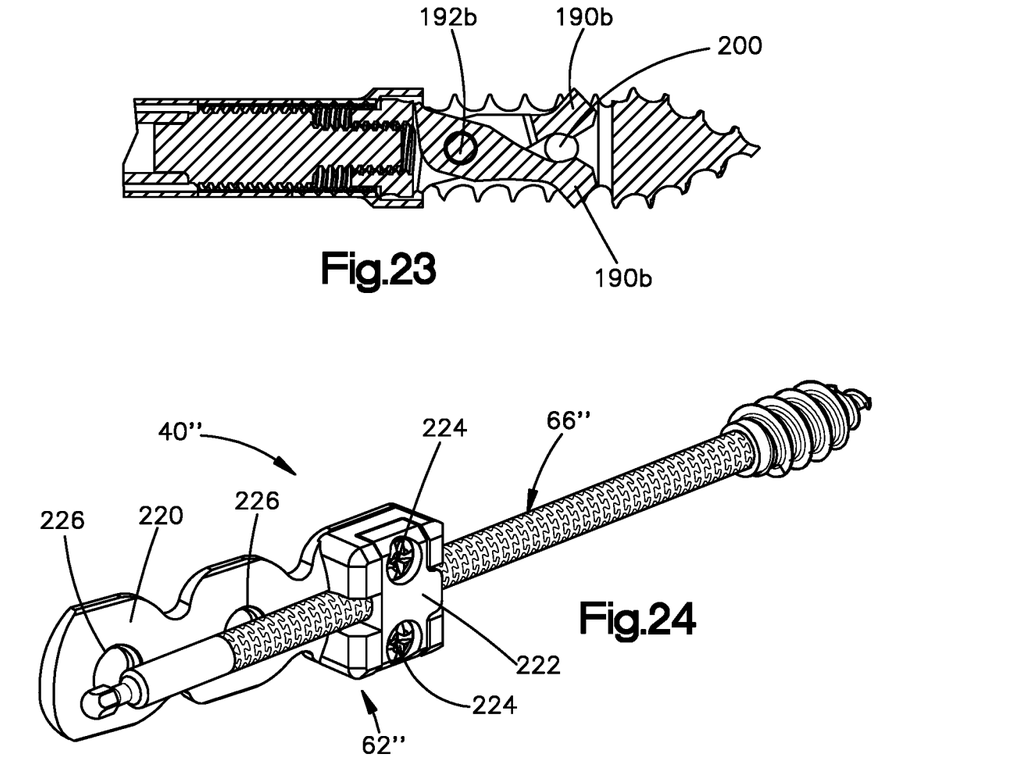
FIG. 23 is a cross-sectional side view of a second embodiment of the distal end of FIG. 22, in an unexpanded configuration.
FIG. 24 is an oblique view of the shaft and distal bone screw of FIG. 1 in combination with a fourth embodiment of the locking member of FIG. 17, including a main lock body and a clamping member.

In some embodiments, the intramedullary bone fixation device 40' includes different configurations of camming arms. For example, camming arms 190b rotatably coupled to pin 192b as shown in FIG. 23. The camming arms 190b have free ends that are disposed distally of the pin 192b when in a retracted position and are configured to rotate into an expanded position. The camming arms may engage a stop 200 when in the retracted position and may be configured to rotate about the pin 192b in a direction opposite to that of the camming arms 190 when rotating into the expanded position.

In an embodiment, the arms and the shaft are configured as a scissor jack such that the shaft is configured as a leadscrew coupled to the arms such that as the leadscrew rotates in one direction the arms expand radially outwardly, and as the leadscrew rotates in an opposite direction the arms retract.

Figure 25:
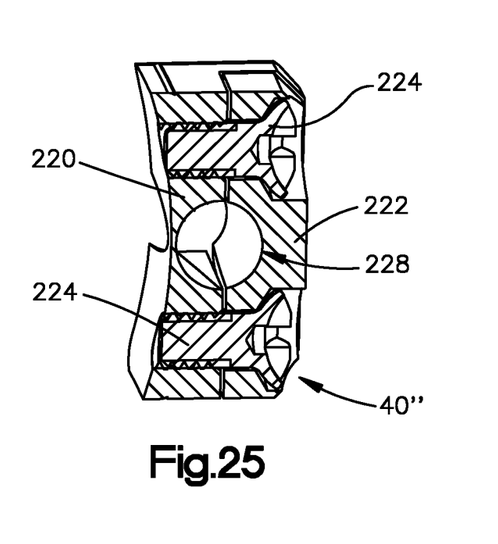
FIG. 25 is a cross-sectional oblique view of the main lock body and the clamping member of FIG. 24.

Referring now to FIGS. 24 and 25, a third embodiment of the intramedullary bone fixation device is shown. It is to be appreciated that the second embodiment can be similar to the above-discussed embodiments of the intramedullary bone fixation device. Accordingly, the same reference numbers used above with reference to the first embodiment can be also used with a "double prime" notation in reference to a third embodiment. It is also to be appreciated that, unless otherwise set forth below, the components (and features thereof) of the intramedullary bone fixation device 40" of the second embodiment can be similar to those above-discussed embodiments.

Referring to FIG. 24, the intramedullary bone fixation device 40" includes a locking member 62" that is configured to attach a shaft 66" to an exterior surface of the first rib segment 44 (FIG. 1). For example, the locking member 62" may include a main lock body 220 configured to contact the first rib segment 44 and clamping member 222 configured to clamp the shaft 66" against the main lock body 220. For example, the locking member 62" includes one or more fasteners 224 that are configured to attach the clamping member 222 to the main lock body 220 such that the shaft 66" is fixedly clamped therebetween.

The main lock body 220 may include fastener holes 226 to receive fasteners (e.g., bone screws) to attach the main lock body 220 to the exterior surface of the first rib segment 44.

Turning to FIG. 25, the main lock body 220 and the clamping member 222 together define a through hole 228 to receive the shaft 66". When the fasteners 224 attach the clamping member 222 to the main lock body 220, the through hole 228 may be sized to clamp or otherwise fix the shaft 66" relative to the main lock body 220. The through hole 228 may be defined by ribbed surfaces (not shown) that are configured to engage recesses of the shaft 66".

Figure 26:
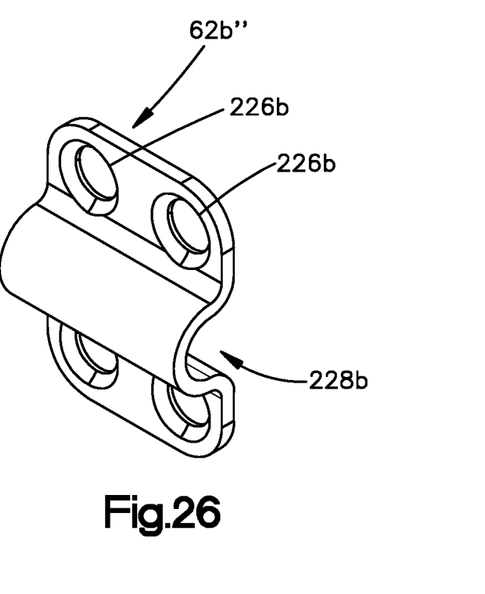
FIG. 26 is an oblique view of a fifth embodiment of the locking member of FIG. 17, including a bone plate.

In some embodiments, the intramedullary bone fixation device 40" includes a different external locking member. For example, the intramedullary bone fixation device 40" may include a locking member 62b" as shown in FIG. 26. The locking member 62b" may be configured to clamp the shaft 66" (FIG. 24) against the exterior of the first rib segment 44 (FIG. 1). The locking member 62b" may be a bone plate that includes fastener holes 226b and a through hole 228b to receive the shaft 66". The through hole 228b may be defined by a ribbed surface (not shown) that is configured to engage recesses of the shaft 66".

Figure 27:
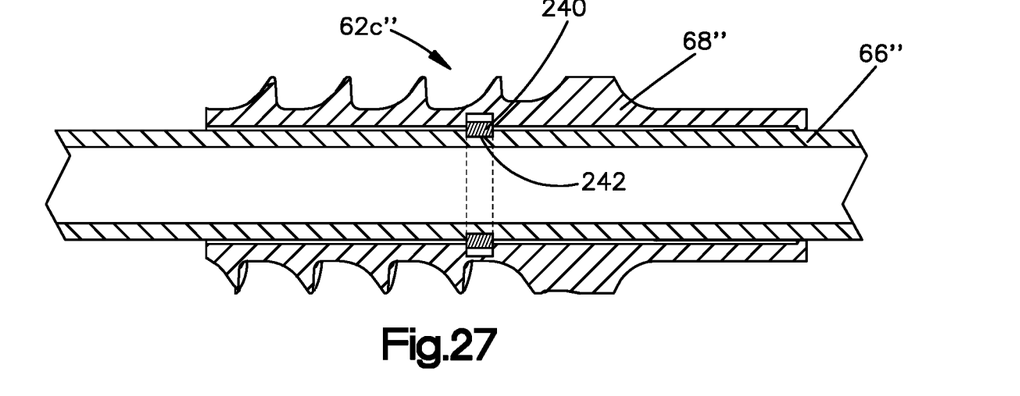
FIG. 27 is a partial cross-sectional side view of a sixth embodiment of the locking member of FIG. 17, including a locking ring.

In an embodiment, the intramedullary bone fixation device 40" includes a different interior or an exterior locking member. For example, the intramedullary bone fixation device 40" includes a locking member 62c", as shown in FIG. 27. The locking member 62c" may include a distal bone screw 68" and a locking ring 240 that is movable with the distal bone screw 68" along the shaft 66" until the locking ring 240 reaches a locking recess 242 of the shaft 66". The locking ring 240 may be configured to contract into the locking recess 242 such that the distal bone screw 68" is axially fixed relative to the shaft 66".

Figure 28:
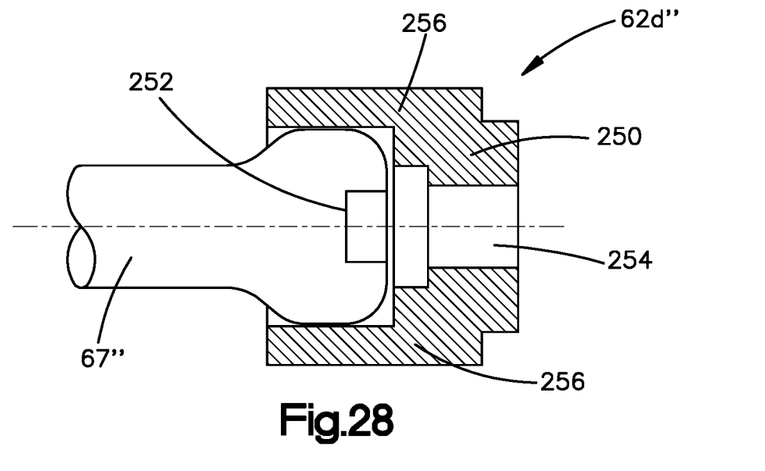
FIG. 28 is a partial cross-sectional side view of a seventh embodiment of the locking member of FIG. 17, including a camming nut.
Figure 29:
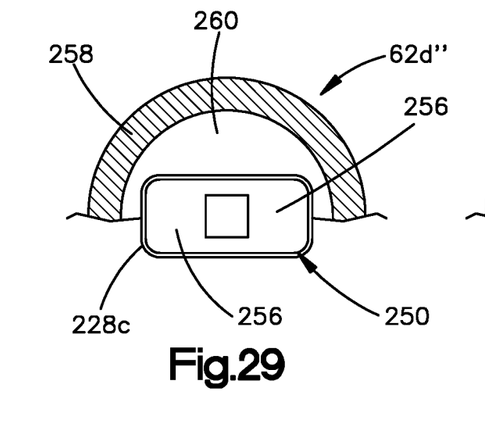
FIG. 29 is a partially cross-sectional rear view of a bone plate in combination with the locking member of FIG. 28, shown in an unlocked configuration.
Figure 30:
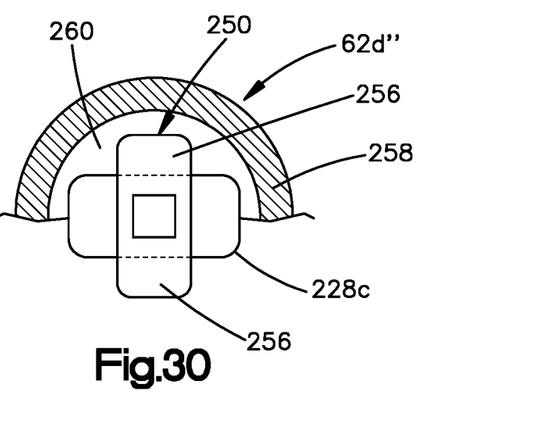
FIG. 30 is a partially cross-sectional rear view of a bone plate in combination with the locking member of FIG. 28, shown in a locked configuration.

In another example, the intramedullary bone fixation device 40" includes a locking member 62d", as shown in FIGS. 28-30. The locking member 62d" may include a tool engagement portion 67" and a camming nut 250 that is configured to rotate relative to the tool engagement portion 67" from an unlocked position shown in FIG. 29 to a locked position shown in FIG. 30. The tool engagement portion 67" may include a tool engagement recess 252 that a tool (not shown) can access via a through hole 254 of the camming nut 250 to rotate the tool engagement portion 67".

As shown in FIGS. 29 and 30, the camming nut 250 may include stop wings 256 that extend radially outwardly. When the camming nut 250 is rotated into the locked position, the stop wings 256 may change orientation such that the stop wings 256 prevent proximal and/or distal movement of the camming nut 250. For example, a mounting bracket 258 (e.g., a bone plate), similar to the locking member 62b" described above, may include a through hole 228c that extends axially and includes an axially intermediate radially enlarged portion 260. The axially intermediate radially enlarged portion 260 provides space for the stop wings 256 to rotate such that the camming nut 250 is in the locked position, and axially adjacent portions of the mounting bracket 258 prevent the stop wings 256 from moving proximally or distally through the through hole 228c. In an embodiment, the camming nut is disposed within the medullary canal.

Certain terminology is used in the following description for convenience only and is not limiting. The words "right", "left", "lower" and "upper" designate directions in the drawings to which reference is made. The words "inner", "internal", and "interior" refer to directions towards the geometric center of the referenced component, while the words "outer", "external", and "exterior" refer to directions away from the geometric center of the implant. The words, "anterior", "posterior", "superior," "inferior," "medial," "lateral," and related words and/or phrases are used to designate various positions and orientations in the human body to which reference is made. When these words are used in relation to a component, they are to be understood as referring to the relative positions of the component when implanted in the body as shown in FIG. 1. The terminology includes the above-listed words, derivatives thereof and words of similar import.

Although the disclosure has been described in detail, it should be understood that various changes, substitutions, and alterations can be made herein without departing from the spirit and scope of the invention as defined by the appended claims. Additionally, any of the embodiments disclosed herein can incorporate features disclosed with respect to any of the other embodiments disclosed herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An intramedullary bone fixation device comprising:
   a shaft having a leading end and a trailing end opposite the leading end;
   a bone screw that extends from the leading end of the shaft, wherein the bone screw is configured to move along a curved medullary canal of a bone; and
   a locking member that includes at least one ratcheting arm that includes at least one protrusion that is configured, when in a locked position, to engage the shaft such that the locking member is movable along the shaft toward the leading end and is not movable along the shaft toward the trailing end,
   wherein the shaft has a flexible region between the leading end and the trailing end, and the flexible region is configured to flex from a first shape to a second shape as the bone screw moves along the curved medullary canal.

2. The intramedullary bone fixation device of claim 1, wherein the shaft is configured to transmit torque from the trailing end to the bone screw via the flexible region.

3. The intramedullary bone fixation device of claim 1, wherein the flexible region includes a plurality of laser cut segments that interlock with one another.

4. The intramedullary bone fixation device of claim 1, wherein when in an unlocked position, the locking member is configured to move along the shaft toward the trailing end and is configured to move along the shaft toward the leading end.

5. The intramedullary bone fixation device of claim 1, wherein the locking member includes radially outer helical threading.

6. The intramedullary bone fixation device of claim 1, wherein the at least one protrusion is at least two radially inwardly extending protrusions configured to engage the shaft when the locking member is in the locked position.

7. The intramedullary bone fixation device of claim 6, wherein the at least two radially inwardly extending protrusions are movable to disengage from the shaft such that the locking member is in an unlocked position, where the locking member is movable toward the trailing end and is movable toward the leading end.

8. The intramedullary bone fixation device of claim 7, wherein the at least one ratcheting arm is a pair of ratcheting arms that each include a respective radially inwardly extending protrusion of the at least two radially inwardly extending protrusions, and wherein the respective radially inwardly extending protrusions are disposed at a distal end of the respective ratcheting arm.

9. The intramedullary bone fixation device of claim 1, wherein the bone screw is configured to ream and purchase with cancellous bone.

10. The intramedullary bone fixation device of claim 1, wherein the flexible region comprises a plurality of segments, and adjacent segments define recesses therebetween, wherein the at least one protrusion is configured to be disposed within least one of the recesses when in the locked position.

11. The intramedullary bone fixation device of claim 1, wherein the flexible region comprises a plurality of segments that are each configured such that adjacent segments are pivotable relative to one another and are inseparable from one another.

12. A method of securing first and second bone segments together, the method comprising the steps of:
    driving a leading end of a bone fixation device through a first portion of a curved medullary canal that is defined by the first bone segment, and into a second portion of the curved medullary canal that is defined by the second bone segment;
    causing a shaft, of the bone fixation device, with a flexible region to flex from a first shape to a second shape during the driving step;
    fixing the leading end to the second bone segment; and
    moving a locking member along the shaft toward the leading end, wherein the locking member includes at least one ratcheting arm that includes at least one protrusion that is in a locked position such that the at least one protrusion engages the shaft, and the locking member is not movable along the shaft toward a trailing end of the shaft that is opposite the leading end.

13. The method of claim 12, further comprising urging the first bone segment toward the second bone segment.

14. The method of claim 13, wherein the locking member urges the first bone segment toward the second bone segment.

15. The method of claim 12, further comprising unlocking the locking member, by moving the at least one protrusion away from the shaft, and moving the locking member away from the leading end along the shaft.

16. The method of claim 15, further comprising moving the locking member within the first portion of the curved medullary canal along the shaft toward the leading end.

17. The method of claim 12, wherein driving the leading end into the first portion comprises inserting an intramedullary bone screw defining the leading end into the first portion.

18. The method of claim 17, further including reaming the first and second portions with the bone screw and purchasing the bone screw with cancellous bone defining the second portion of the curved medullary canal.

19. The method of claim 12, further comprising inserting a resorbable or non-resorbable adhesive or polymer into the shaft such that the adhesive or polymer secures the shaft to the first and second bone segments.

20. The method of claim 19, wherein the adhesive or polymer is a cyanoacrylate, calcium phosphate, or poly (L/DL-lactide).

* * * * *